US005750785A

United States Patent [19]

Matsushima et al.

[11] Patent Number: 5,750,785

[45] Date of Patent: May 12, 1998

[54] 1,4-BIS(2', 2'-DIPHENYLVINYL)BENZENE DERIVATIVE AND CHARGE TRANSPORTING MATERIAL AND ELECTROPHOTOGRAPHIC PHOTORECEPTOR USING THE SAME

[75] Inventors: Yoshimasa Matsushima; Hiroshi Sugiyama; Toshimitsu Hagiwara, all of Kanagawa, Japan

[73] Assignee: Takasago International Corporation, Tokyo, Japan

[21] Appl. No.: 597,806

[22] Filed: Feb. 7, 1996

Related U.S. Application Data

[62] Division of Ser. No. 233,433, Apr. 28, 1994, Pat. No. 5,521,042.

[30] Foreign Application Priority Data

Apr. 28, 1993 [JP] Japan ........ 5-123106

[51] Int. Cl.$^6$ ........ C07C 211/54

[52] U.S. Cl. ........ 564/315

[58] Field of Search ........ 564/315

[56] References Cited

U.S. PATENT DOCUMENTS 4,971,874 11/1990 Ueda ........ 430/58
5,077,162 12/1991 Ueda ........ 430/59
5,250,377 10/1993 Shimada et al. ........ 430/59
5,488,601 1/1996 Sakano et al. ........ 369/120
5,629,920 5/1997 Sakano et al. ........ 369/120

OTHER PUBLICATIONS

Aoki et al., Chemical Abstracts, vol. 122, abstract 147558, 1995.

*Primary Examiner*—Richard L. Raymond
*Attorney, Agent, or Firm*—Sughrue, Mion, Zinn, Macpeak & Seas, PLLC

[57] ABSTRACT

A 1,4-bis(2',2'-diphenylvinyl)benzene derivative represented by formula (I):

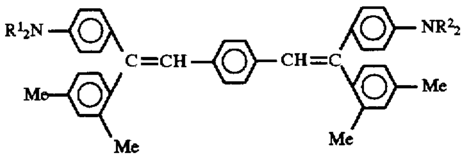

(I)

wherein $R^1$ and $R^2$ each represents a different lower alkyl group and Me represents a methyl group, a charge transporting material containing the compound (I), and an electrophotographic photoreceptor comprising a charge transporting layer containing the charge transporting material are disclosed.

12 Claims, No Drawings

1,4-BIS(2', 2' -DIPHENYLVINYL)BENZENE DERIVATIVE AND CHARGE TRANSPORTING MATERIAL AND ELECTROPHOTOGRAPHIC PHOTORECEPTOR USING THE SAME

This is a divisional of application Ser. No. 08/233,433 filed Apr. 28, 1994, now U.S. Pat. No. 5,521,042.

FIELD OF THE INVENTION

The present invention relates to a novel compound, 1,4-bis(2',2',-diphenylvinyl)benzene derivative represented by the following formula (I), a charge transporting material containing the novel compound, and an electrophotographic photoreceptor comprising a charge transporting layer containing the charge transporting material:

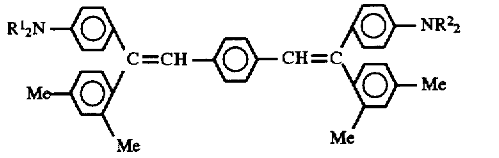

(I)

wherein $R^1$ and $R^2$ each represents a different lower alkyl group and Me represents a methyl group.

BACKGROUND OF THE INVENTION

Recently, as an inorganic photoconductive material, amorphous silicon, amorphous selenium, cadmium sulfide, zinc oxide, etc., are used, but some of these materials are expensive owing to the difficulty of the production thereof and some of them cause a problem from the view point of an environmental protection owing to the toxicity of them.

On the other hand, as an organic photoconductive material, in particular, a function-separating type light-sensitive material comprising a composition of a charge generating material and a charge transporting material has been positively proposed (e.g., U.S. Pat. No. 3,791,826). In the system, by using a material showing a high carrier generation efficiency as the charge generating material and combining the charge generating material and a material having a high charge transportability as a charge transporting material, there is a possibility of obtaining an electrophotographic photoreceptor having a high sensitivity.

In these materials, the charge transporting material is required to efficiently receive carriers generated in the charge generating material by the irradiation of light under the application of an electric field, quickly transport the carriers in the photoreceptor layer, and quickly erase the charge on the surface.

The transferring velocity of a carrier per unit electric field is called a carrier drift mobility. A high carrier drift mobility means that the carrier transfers quickly in the charge transporting layer.

The carrier drift mobility is specific to the charge transporting material, and hence in order to attain the high carrier drift mobility, it is necessary to use a material showing a high carrier drift mobility. The carrier drift mobility by the conventional materials has not yet reached a sufficient level at present.

On the other hand, since the carrier drift mobility depends upon the concentration of the charge transporting material, a method of increasing the concentration of a charge transporting material in a charge transporting layer is employed. The case that the concentration of a charge transporting material becomes the highest is the case that the charge transporting layer is formed by the charge transporting material only and such a charge transporting layer is formed by a vapor deposition method, etc. For example, an organic electroluminescence (EL) device, etc., is prepared by the method as described above [e.g., C. W. Tang and S. A. VanSlyke, *Appl. Phys. Lett.*, 51, 913(1987)].

However, when the thin layer is a vapor-deposited layer composed of a charge transporting material only, in particular, crystals are liable to deposit and pin holes are liable to form, whereby it is difficult to form the layer having a uniform quality.

Also, when an organic solvent solution containing a charge transporting material at a high concentration together with a binder polymer is coated to form a coated layer, it is necessary to form a uniform organic thin layer having no deposition of crystals and no formation of pin holes. This is because since a high electric field is applied to the thin layer formed, if the thin layer has fine crystals or pin holes, a dielectric breakdown occurs at the positions of forming the fine crystals or pin holes to cause noise.

Also, even when the characteristics of both the charge generating material and the charge transporting material are good, it is important that the injection of carriers from the charge generating material into the charge transporting material, that is, the injection of carriers from the charge generating layer into the charge transporting layer be carried out with a good efficiency. The injection of the carriers depends upon the characteristics of the interface between a charge generating material (or a charge generating layer) and a charge transporting material (or a charge transporting layer) and hence the injection of the carriers varies between the kinds of the materials being used. As described above, various conditions are required for a charge transporting material.

Hitherto, as a charge transporting material, for example, a distyryl compound represented by the following formula (II) is proposed in JP-A-63-269158 (the term "JP-A" as used herein means an "unexamined published Japanese patent application"):

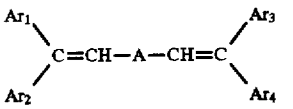

(II)

wherein $Ar_1$ to $Ar_4$ each independently represents an alkyl group, an aralkyl group, an aromatic hydrocarbon group which may have a substituent, or an aromatic heterocyclic group which may have a substituent and A represents an alkyl group, an aralkyl group, an aryl group or a heterocyclic group, wherein each group may have a substituent.

Also, JP-A-3-11355 discloses a distyryl compound represented by the following formula (III):

(III)

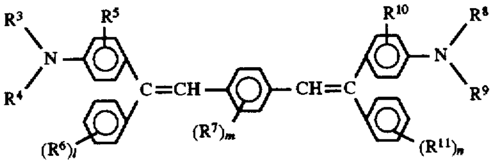

wherein $R^3$, $R^4$, $R^8$, and $R^9$ each independently represents an alkyl group, an aralkyl group, or an aryl group which each may have a substituent; $R^5$, $R^7$, and $R^{10}$ each independently represents a hydrogen atom, an alkyl group, an alkoxy group, or a halogen atom; $R^6$ and $R^{11}$ each represents an alkyl group or an alkoxy group; l and n each represents an integer of from 1 to 3; and m represents an integer of from 0 to 2.

However, in the compounds which were obtained in the Examples or were actually described in the specification, the dialkylamino group substituted on both terminals thereof is the same and there are problems that the compound is insufficient in the point of solubility in a binder polymer and even when the compound is dissolved in a binder polymer, when a film or layer is formed using it, crystallization occurs, pin holes form, and the film or layer is whitened or becomes brittle, which results in forming defects on the images formed, and hence there is a restriction on the addition amount of the compound.

SUMMARY OF THE INVENTION

The object of the present invention is to provide a new material as a charge transporting material, which has a good solubility in a binder polymer, is stable in the case of forming a film even when the addition amount is increased, which can thus show a high carrier drift mobility, and is excellent in various characteristics (e.g., high sensitivity and low residual potential) in the case of forming an electrophotographic photoreceptor.

As the result of making various investigations on various compounds, the present inventors have discovered that the object described above can be attained by a 1,4-bis(2',2'-diphenylvinyl)benzene derivative represented by the following formula (I) having a different dialkylamino group at both the terminals and have succeeded in accomplishing the present invention based on this discovery:

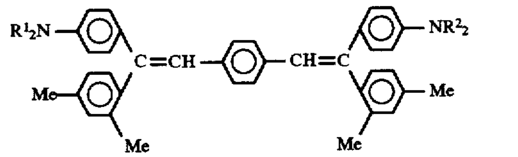

(I)

wherein $R^1$ and $R^2$ each represents a different lower alkyl group and Me represents a methyl group.

Thus, according to an aspect of the present invention, there is provided the novel 1,4-bis(2',2'-diphenylvinyl) benzene derivative represented by the formula (I) described above.

According to another aspect of the present invention, there is provided a charge transporting material containing the compound shown by the formula (I) described above.

According to still another aspect of the present invention, there is provided an electrophotographic photoreceptor comprising a charge transporting layer containing the charge transporting material.

DETAILED DESCRIPTION OF THE INVENTION

Then, present invention is now described in detail.

In the compound of the present invention shown by the formula (I) described above, $R^1$ and $R^2$ each represents a different lower alkyl group and although there is no particular restriction on the lower alkyl group, a lower alkyl group having from 1 to 4 carbon atoms is preferred. Specific examples of the preferred lower alkyl group are methyl, ethyl, propyl, and n-butyl.

Furthermore, as specific examples of the more preferred compound of the present invention shown by the formula (I), there are the compounds shown by Table 1 below but the compounds of the formula (I) are not limited to these compounds.

TABLE 1

| Illustrative Compound | $R^1$ | $R^2$ |
|---|---|---|
| 1 | Me | Et |
| 2 | Me | Pr |
| 3 | Me | Bu |
| 4 | Et | Pr |
| 5 | Et | Bu |
| 6 | Pr | Bu |

In the above table, Me represents a methyl group, Et an ethyl group, Pr a propyl group, and Bu an n-butyl group.

The 1,4-bis(2',2'-diphenylvinyl)benzene derivative of the present invention shown by the formula (I) described above can be easily synthesized according to, for example, the following reaction scheme 1:

Reaction Scheme 1:

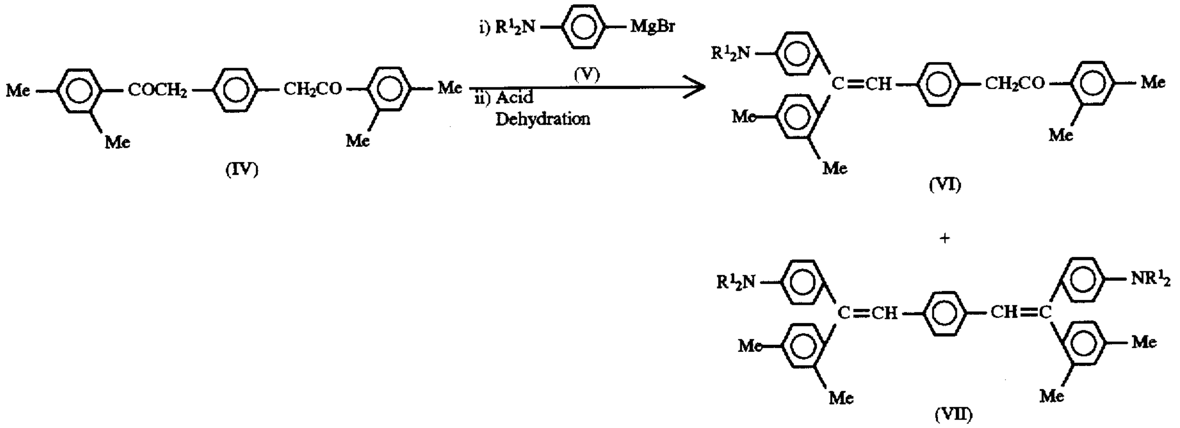

(IV) (VI) + (VII)

-continued

Reaction Scheme 1:

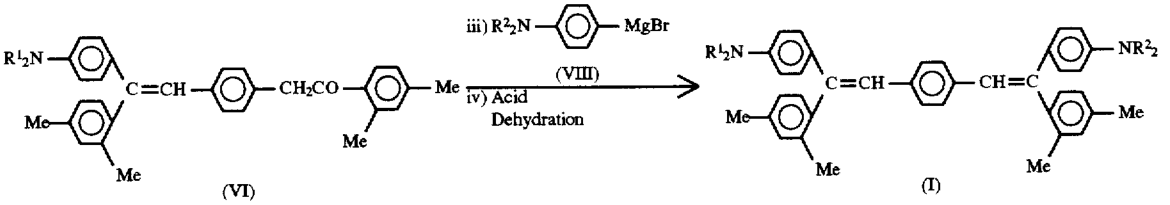

(VI) (I)

In the above formulae, $R^1$, $R^2$, and Me have the same meaning as described above.

That is, i) 1,4-bis(2,4-dimethylbenzoylmethyl)benzene (IV) reacts with the first Grignard reagent (V) obtained from 1-dialkyl-4-bromobenzene and ii) then, if necessary, the product obtained is subjected to a dehydration reaction in the presence of an acid catalyst to provide the monoketone compound (VI).

iii) By the reaction of the monoketone compound (VI) with the second Grignard reagent (VIII) and iv) then, if necessary, by subjecting the product thus obtained to a dehydration reaction in the presence of an acid catalyst, the 1,4-bis(2',2'-diphenylvinyl)benzene derivative (I) can be easily obtained.

Now, the starting compound, 1,4-bis(2,4-dimethylbenzoylmethyl)benzene (IV) can be easily synthesized according to the following reaction scheme 2 as shown, e.g., in K. Sakamoto et al, *Bulletin of the Chemical Society of Japan*, Vol. 46, 270–275(1973).

Reaction Scheme 2:

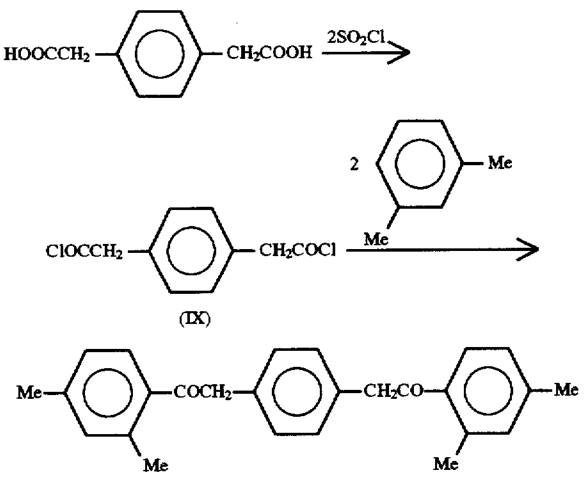

(IX)

(IV)

That is, p-phenylene diacetic acid reacts with thionyl chloride (IX) to provide the acid chloride (IX) and by subjecting the acid chloride (IX) and m-xylene to a Friedel-Crafts reaction, the compound (IV) can be easily obtained.

The usefulness of the compound (I) of the present invention obtained as described above is now explained.

The conventional compounds obtained in the Examples or actually described in JP-A-3-11355, etc., each has the same dialkylamino group at both the terminals of the compound. Such a 1,4-bis(2',2'-diphenylvinyl)benzene compound having the same dialkylamino group at both the terminals thereof has a high crystallizability, and in a molecular thin film composed of the compound itself formed by a method such as a vapor deposition, etc., and in a thin film having dispersed therein such compound at a high concentration formed using a binder polymer, the deposition of fine crystals occurs, which causes the occurrence of defects in the images formed.

However, in the case of using the compound (I) of the present invention obtained as described above, that is, the 1,4-bis(2',2'-diphenylvinyl)benzene derivative having a different dialkylamino group at both the terminals thereof, in the molecular thin film composed of the compound itself formed by a method such as a vapor deposition and in the thin film having dispersed therein the compound at a high concentration formed using a binder polymer, the deposition of fine crystals does not occur and the film obtained is uniform in quality and stable.

Such a difference in crystallizability is clarified in the measurement using, for example, a differential scanning calorimeter (DSC). That is, in the glass transition temperature (Tg), the crystallization temperature (Tc), and the melting point (Tm) measured by the differential scanning calorimeter (DSC), the condition of being difficult to crystallize depends on the following matters as a whole.

That is, (1) the crystallization temperature (Tc) can not be measured (i.e., not crystallized) or as the crystallization temperature (Tc) is higher, the crystallization occurs with more difficulty; (2) as the difference (Tc–Tg) between the crystallization temperature and the glass transition temperature is larger, the crystallization occurs with more difficulty; (3) as the difference (Tm–Tc) between the melting point and the crystallization temperature is smaller, the crystallization occurs with more difficulty; and (4) as the glass transition temperature (Tg) is higher, the crystallization occurs with more difficulty.

That is, as will be understood from Test Example 1 described hereinbelow, it can be seen that in the conventional 1,4-bis(2',2'-diphenylvinyl)benzene compound having the same dialkylamino group at both terminals thereof, in the DSC analysis, with the increase of the temperature, the glass transition temperature, the crystallization temperature, and the melting point are observed and the crystallization temperature is lower than the glass transition temperature, that is, a stable temperature range as the molecular solid solution is narrow.

However, in the compound of the present invention, i.e., the 1,4-bis(2',2'-diphenylvinyl)benzene derivative (I) having a different dialkylamino group at both terminals thereof, it can be seen that in the DSC analysis, as the case may be, the crystallization temperature is not observed or the crystallization temperature is higher than the glass transition temperature, i.e., the stable temperature range as the molecular solid solution is broad. Accordingly, in the case of containing the compound (I) of the present invention, the stable and uniform thin film can be formed without being accompanied by the deposition of crystals.

The compound (I) of the present invention has excellent properties as a charge transporting material and by using the compound (I) of the present invention, an electrophotographic photoreceptor having a high carrier drift mobility, a high sensitivity, and causing no residual potential can be obtained.

Practically, in an electrophotographic photoreceptor comprising an electrically conductive substrate having formed thereon a photosensitive layer including a charge generating layer and a charge transporting layer, the compound (1) of the present invention is used for the charge transporting layer as a charge transporting material.

The charge transporting layer of the present invention can be formed as a molecular thin film of the compound (I) of the present invention by vapor depositing the compound (I) as it is or by coating a solution obtained by dissolving the compound (I) in a proper solvent followed by drying.

Or, in the case of requiring mechanical strength, etc., the charge transporting layer is formed by coating a solution obtained by dissolving the compound (I) of the present invention in a proper solvent together with a binder on an electrically conductive substrate or a charge generating layer formed on the substrate followed by drying.

As the binder being used in such a case, there are, for example, polyacrylate, polyamide, polymethacrylate, a polyvinyl chloride resin, a polyvinyl acetate resin, an epoxy resin, a polyester, polycarbonate, polyurethane, polystyrene, and the copolymers of them. Also, as other polymers than the insulating polymers as described above, organic photoconductive polymers such as polyvinylcarbazole, polyvinylanthracene, polyvinylene, etc., can be used.

There is no particular restriction on the compounding ratio of the binder and the compound (I) of the present invention and they may be compounded with an optional ratio but it is desirable that the amount of compound (I) of the present invention is as large as possible.

Practically, the compounding amount of the compound (I) of the present invention can be from 10 to 1,000 parts by weight to 100 parts by weight of the binder. That is, in the case of using a conventional charge transporting material, when more than about 2 parts by weight of the charge transporting material are used to 1 part by weight of a binder, there is a problem about the stability of the layer formed, but in the case of using the compound (I) of the present invention, even when about 10 parts by weight of the compound (I) of the present invention are added to 1 part by weight of the binder, the layer formed is uniform and stable.

There is no particular restriction about the solvent being used but organic solvents can be used. That is, alcohols such as methanol, ethanol, isopropanol, etc.; ketones such as acetone, methyl ethyl ketone, cyclohexanone, etc., amides such as N,N-dimethylformamide, N,N-dimethylacetamide, etc.; sulfoxides such as dimethylsulfoxide, etc.; ethers such as tetrahydrofuran, dioxane, ethylene glycol dimethyl ether, etc.; esters such as ethyl acetate, methyl acetate, etc.; aliphatic halogenated hydrocarbons such as methylene chloride, chloroform, 1,2-dichloroethane, dichloroethylene, carbon tetrachloride, trichloroethylene, etc.; and aromatic compounds such as benzene, toluene, xylene, chlorobenzene, dichlorobenzene, etc., can be used.

As the electrically conductive substrate being used for the electrophotographic photoreceptor of the present invention, a sheet-form or drum-form foil or plate of a metal such as copper, aluminum, silver, iron, zinc, nickel, etc., or an alloy thereof is used. Also, a plastic film or cylinder vacuum evaporated or electrolytically plated with the foregoing metal or a substrate such as a glass, a paper or a plastic film having formed thereon a layer of an electrically conductive compound such as an electrically conductive polymer, indium oxide, tin oxide, etc., by coating or by a vapor-deposition is used as the electrically conductive substrate.

Coating for preparing the charge transporting layer described above can be carried out using a dip coating method, a spray coating method, a spinner coating method, a wire bar coating method, a blade coating method, a roller coating method, a curtain coating method, etc.

Drying of the coated layer is preferably carried out by a method of drying by heating after drying at room temperature. Drying by heating is preferably carried out in the range of a temperature of from 30° C. to 200° C. for from 5 minutes to 2 hours under a windless state or under air blowing.

Furthermore, if necessary, the charge transporting layer in the present invention may contain various additives. For example, plasticizers such as biphenyl, dibutyl phthalate, etc.; surface lubricants such as silicone oils, graft type silicone polymers, various fluorocarbons, etc.; electric potential stabilizers such as dicyanovinyl compounds, carbazole derivatives, etc.; monophenol series antioxidants such as 2-tert-butyl-4-methoxyphenol, etc.; bisphenol series antioxidants; amine series antioxidants such as 1,4-diazabicyclo[2.2.2]octane; and salicylic acid series antioxidants can be added.

Also, if necessary, other charge transporting materials can be added to the charge transporting layer in the present invention.

The thickness of the charge transporting layer formed is from 2 to 40 μm, and preferably from 5 to 30 μm.

By electrically connecting the charge transporting layer obtained to a charge generating layer, the charge transporting layer can have the function of receiving the carriers injected from the charge generating layer in the existence of an electric field and transporting the carriers to the surface of the photosensitive layer.

In this case, the charge transporting layer may be laminated on the charge generating layer or under the charge generating layer but it is preferred that the charge transporting layer is laminated on the charge generating layer.

In the photosensitive layer in the present invention, if necessary, a protective layer may be formed on the layer thus formed.

As the charge generating layer used in the present invention, a vapor-deposited layer or a coated layer formed by using an inorganic charge generating material such as selenium, selenium-tellurium, amorphous silicon, etc., or an organic charge generating material such as cationic dyes (e.g., pyrylium salt series dyes, thiapyrylium salt series dyes, azulenium salt series dyes, thiacyanine series dyes, and quinocyanine series dyes), squarylium salt series pigments, phthalocyanine series pigments, anthanthrone series pigments, polycyclic quinone pigments (e.g., dibenzpyrene quinone series pigments and pyranthrone series pigments), indigo series pigments, quinacridone series pigments, azo pigments, pyrrolopyrrole series pigments, etc., can be used. In addition to these materials described above, any materials which absorb light and generate carriers at a high efficiency can be used.

In the manner as described above, the electrophotographic photoreceptor containing the 1,4-bis(2',2'-diphenylvinyl) benzene derivative shown by the formula (I), i.e., the compound (I) of the present invention, in the charge transporting layer can be obtained.

The 1,4-bis(2',2'-diphenylvinyl)benzene derivative (I) of the present invention has the advantages that the compound can form a stable amorphous thin film or layer and has a high carrier drift mobility, and can be widely used not only for the electrophotographic photoreceptor but also as charge transporting materials such as an organic electroluminescence (EL) material, etc.

The following examples are intended to illustrate the present invention more in detail but not to limit it in any way.

In addition, the measurement apparatus and the measurement conditions used in the examples are shown below.

(1) $^1$H-NMR

Apparatus: AM-400 Type Apparatus (trade name, manufactured by Bruker, Inc.) (400 MHz).

Solvent: $CDCl_3$

Internal standard substance: tetramethylsilane (2) IR

Apparatus: IR-810 Type Infrared Spectrometer (trade name, manufactured by JASCO Inc.)

(3) MASS

Apparatus: Hitachi M-80B (trade name, manufactured by Hitachi, Ltd.)

Ionization Chamber Temperature: 200° C.

Ionization Voltage: 20 eV (3) Differential Scanning Calorimeter (DSC)

Apparatus: SSC-5220 Apparatus (trade name, manufactured by Seiko Instruments, Inc.)

SYNTHESIS EXAMPLE

Synthesis of 1,4-bis(2',4'-dimethylbenzoylmethyl) benzene

A mixed solution of 20 g (0.103 mol) of p-phenylene diacetic acid, 40 ml (0.551 mol) of thionyl chloride, and 200 ml of methylene chloride was refluxed with stirring for 24 hours and after cooling the reaction mixture was filtered to remove unreacted p-phenylene diacetic acid. The filtrate was condensed and the condensed product was dissolved in 100 ml of methylene chloride to form a solution 1.

In a 500 ml reaction flask was placed 100 ml of methylene chloride and then 32 g (0.24 mol) of anhydrous aluminum chloride was added thereto at 0° C. over a period of 30 minutes. Then, 22 g (0.207 mol) of m-xylene was added dropwise to the mixture at the same temperature and further, the solution 1 formed above was added at a temperature of from 0° C. to 5° C. over a period of 30 minutes. After carrying out the reaction of the solution for one hour at the same temperature and for 30 minutes at room temperature, the reaction mixture was poured into ice-water, extracted with benzene, and the extract was washed with an aqueous sodium carbonate solution, dried, and concentrated to provide 35 g of a crude product, which was recrystallized from ethanol to obtain 14 g of the crystals of 1,4-bis(2',4'-dimethylbenzoylmethyl)benzene (theoretical yield 36.4%).

M.p.: 94° C. to 96° C.

IR ($cm^{-1}$): 1680

Comparative Example 1

Preparation of 1-[β-(2',4'-dimethylphenyl)-β-(4'-dipropylaminophenyl)vinyl]-4-(2',4'-dimethylbenzoylmethyl)benzene and 1,4-bis[β-(2',4'-dimethylphenyl)-β-(4'-dipropylaminophenyl)vinyl]benzene (Comparative Compound 1):

In a 5 liter reaction flask were placed 33.64 g (1.384 mol) of magnesium and 50 ml of dry tetrahydrofuran (THF) under a nitrogen gas atmosphere and then small amounts of iodine and ethyl bromide were added thereto. After confirming the initiation of the reaction, a mixed solution of 337.69 g (1.305 mol) of N,N-dipropyl-p-bromoaniline and 1268 ml of dry THF was added dropwise to the mixture at a temperature of from 25° C. to 35° C. over a period of 2 hours. Thereafter, the reaction was carried out for 18 hours at room temperature to provide a Grignard reagent.

Then, to the reaction mixture was added dropwise a mixed solution of 199.32 g (0.514 mol) of 1,4-bis(2',4'-dimethylbenzoylmethyl)benzene synthesized in Synthesis Example and 1318 ml of toluene at a temperature of from 23° C. to 35° C. over a period of 2 hours. Then, after stirring the mixture for 3 hours at room temperature and refluxing for 25 hours at 81° C., 2 liters of toluene was added thereto and after removing THF at atmospheric pressure (boiling point to 104° C., 2 liters), the mixture was heated at 107° C. for 16 hours with stirring.

After cooling, the reaction mixture was poured into 2961 g of an ice-cooled aqueous 5% ammonium chloride solution and the mixture was stirred for 30 minutes under cooling. Thereafter, 2 liters of toluene was added to the mixture, the mixture was filtered with sellite, the filtrate was separated, washed with an aqueous sodium chloride solution (1.5 liters, twice, pH after washing was 7), dried with anhydrous magnesium sulfate, and concentrated to provide 443.44 g of a mixture of a crude monool substance A, (1-[2-hydroxy-2-(2',4'-dimethylphenyl)-2-(4'-dipropylaminophenyl)ethyl]-4-(2',4'-dimethylbenzoylmethyl)benzene) and a crude diol substance A (1,4-bis[2-hydroxy-2-(2',4'-dimethylphenyl)-2-(4'-dipropylaminophenyl)ethyl]benzene shown below.

Monool Substance A

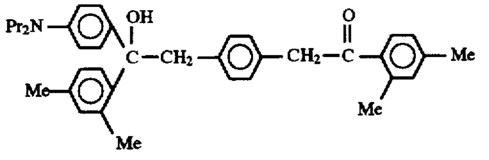

Diol Substance A

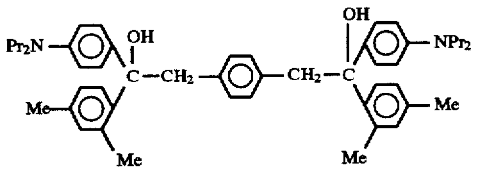

In a 5 liter reaction flask were placed 443.44 g of the mixture obtained as described above, 1330 ml of toluene, and 22.2 g of p-toluenesulfonic acid (PTSA) and the azeotropic dehydration reaction was carried out for 4 hours under refluxing (112° C.).

After cooling, the reaction mixture was washed with an aqueous sodium chloride solution (2.5 liters, twice, pH after washing was 4), washed with an aqueous 5% sodium carbonate solution (2.5 liters), washed with an aqueous sodium chloride solution (2.5 liters, 3 times, pH after washing was 7), dried with anhydrous sodium sulfate, and concentrated to provide 424.07 g of a mixture of a crude monoketone substance A, (1-[β-(2',4'-dimethylphenyl)-β-(4'-dipropylaminophenyl)vinyl]-4-(2',4'-dimethylbenzoylmethyl)benzene) and a crude diene substance A, (1,4-bis[β-(2',4'-dimethylphenyl)-β-(4'-dipropylaminophenyl)vinyl]benzene) shown below.

Monoketone Substance A

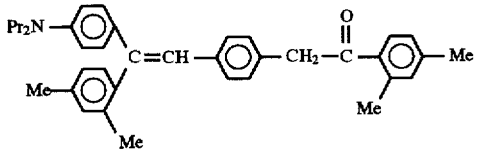

Diene Substance A

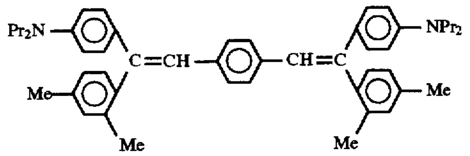

The mixture was distilled (boiling point to 87° C./1 mmHg, bath temperature to 160° C.) by a Vigreux distilling column to remove 80.12 g of N,N-dipropylaniline to provide 315.17 g of a residue. To the residue was added 2521 ml of ethanol and the mixture was refluxed for 3 hours at 79° C. with stirring under the irradiation of an incandescent lamp. The hot reaction mixture was filtered under reduced pressure and 103.42 g of the diene substance A was collected by filtration (the crystals were defined as the 1st crystals). The 1st mother liquor was purified by silica gel column chromatography (eluent: benzene) to provide 85.27 g (theoretical yield of 28.0%) of the oily monoketone substance A, (1-[β-(2',4'-dimethylphenyl)-β-(4'-dipropylaminophenyl)vinyl]-4-(2',4'-dimethylbenzoylmethyl)benzene) which was the desired compound formed by reacting 1 mol only of the Grignard reagent to the substrate.

MASS (m/z): 529 ($M^+$)

IR (neat, $cm^{-1}$): 1680 (C═O)

$^1$H-NMR (400 MHz, δppm, $CDCl_3$); 0.91(6H, t, J=7.4 Hz), 1.60(4H, m), 2.01(3H, s), 2.33(3H, s), 2.37(3H, s), 2.41(3H, s), 3.23(4H, t, J=7.6 Hz), 4.07(2H, s), 6.56(2H, d, J=8.9 Hz), 6.85(2H, d, J=8.2 Hz), 6.89(1H, s), 6.96(2H, d, J=8.2 Hz), 6.97 to 7.05(5H, m), 7.15(2H, d, J=8.9 Hz), 7.60(1H, d, J=8.4 Hz)

The 1st crystals obtained by filtration were purified by silica gel column chromatography (eluent: benzene) and recrystallized from 334 ml of ethanol to provide 94.94 g of the diene substance A. Furthermore, the 1st mother liquor was purified by silica gel column chromatography (eluent: benzene) and recrystallized to provide 38.19 g of the diene substance A.

Thus, the sum total of 133.13 g of the diene substance A, i.e., 1,4-bis[β-(2',4'-dimethylphenyl)-β-(4'-dipropylaminophenyl)vinyl]benzene (Comparative Compound 1) (theoretical yield of 37.2%) shown below.

Diene Substance A

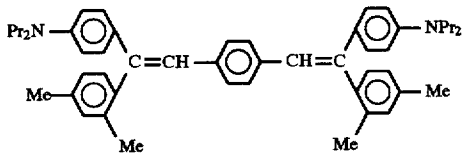

M.p.: 172° C. to 173° C.

MASS (m/z): 688, 358

$^1$H-NMR Spectra (400 MHz, δppm, $CDCl_3$); 0.90(12H, t, J=7.4 Hz), 1.58(8H, m), 1.98(6H, s), 2.36(6H, s), 3.21(8H, t, J=7.7 Hz), 6.53(4H, d, J=9.1 Hz), 6.64(4H, s), 6.80(2H, s), 6.95(2H, d, J=7.7 Hz), 6.99(2H, d, J=7.8 Hz), 7.03(2H, s), 7.10(4H, d, J=9.1 Hz)

EXAMPLE 1

Preparation of 1-[β-(2',4'-dimethylphenyl)-β-(4'-dipropylaminophenyl)vinyl]-4-[β-(2',4'-dimethylphenyl)-β-(4'-diethylaminophenyl)vinyl]benzene (Illustrative Compound 4)

In 2 liter reaction flask were placed 7.12 g (0.292 mol) of magnesium and 9 ml of a mixed solvent of dry THF and toluene (volume ratio of 405:111) under a nitrogen atmosphere, and small amounts of iodine and ethyl bromide were added to the mixture. After confirming the initiation of the reaction, a mixed solution of 64.38 g (0.282 mol) of N,N-diethyl-p-bromoaniline and 507 ml of the mixed solvent described above was added dropwise to the mixture at a temperature of from 25° C. to 45° C. over a period of 0.5 hour. Thereafter, the reaction was carried out for 3 hours at 45° C. to provide a Grignard reagent.

Then, to the reaction mixture was added dropwise a mixed solution of 67.09 g (0.105 mol) of the monoketone substance A, (1-[β-(2',4'-dimethylphenyl)-β-(4'-dipropylaminophenyl)vinyl]-4-(2',4'-dimethylbenzoylmethyl)benzene and 134 ml of dry toluene at a temperature of from 23° C. to 30° C. over a period of 0.5 hour and after carrying out the reaction for 19 hours at room temperature, the reaction mixture was poured into 603 g of an ice-cooled aqueous 5% ammonium chloride solution. After stirring the solution for 30 minutes,, the solution containing the product was separated, washed with an aqueous sodium chloride solution, dried with anhydrous magnesium sulfate, and concentrated to provide 106.92 g of a crude monool substance B, (1-[β-(2',4'-dimethylphenyl)-β-(4'-dipropylaminophenyl)vinyl]-4-[2-hydroxy-2-(2',4'-dimethylphenyl)-2-(4'-diethylaminophenyl)ethyl]benzene shown below.

Monool Substance B

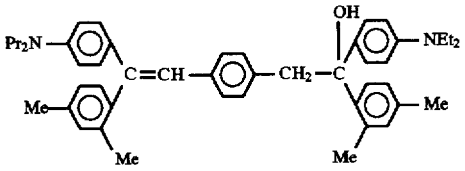

In one liter reaction flask were placed 106.9 g of the crude monool substance B described above, 427.68 ml of toluene, and 2.12 g of PTSA and the mixture was subjected to an azeotropic dehydration reaction for 2 hours under refluxing (112° C.). After cooling, the reaction mixture was washed with an aqueous sodium chloride solution, washed with an aqueous 1% sodium carbonate solution, washed again with an aqueous sodium chloride solution, dried, and concentrated to provide 101.25 g of a crude product. The crude product was distilled (boiling point to 96° C./1 mmHg, bath temperature to 160° C.) by a Vigreux distilling column to remove 11.19 g of N,N-diethylaniline. Then, 85.71 g of the residue formed was purified by silica gel column chromatography (eluent:benzene) and then dissolved in 106 ml of hot ethyl acetate by heating. Furthermore, 424 ml of hot ethanol was added to the solution and after allowing to cool the mixture, the product was recrystallized to provide 24.39 g of 1-[β-(2',4'-dimethylphenyl)-β-(4'-dipropylaminophenyl)vinyl]-4-[β-(2',4'-dimethylphenyl)-β-(4'-diethylaminophenyl)vinyl]benzene (Illustrative Compound 4).

M.p.: 136° C. to 137° C.

MASS (m/z): 660 ($M^+$)

$^1$H-NMR (400 MHz, δppm, $CDCl_3$): 0.90(6H, t, J=7.4 Hz), 1.14(6H, t, J=7.0 Hz), 1.58(4H, q, J=7.5 Hz), 1.98(6H, s), 2.36(6H, s), 3.21(4H, q, J=7.5 Hz), 3.33(4H, q, J=7.0 Hz), 6.53(2H, d, J=9.0 Hz), 6.57(2H, d, J=9.0 Hz), 6.64(4H, s), 6.80(2H, s), 6.95(2H, d, J=7.7 Hz), 6.99(2H, d, J=7.8 Hz), 7.03(2H, s), 7.11(2H, d, J=9.0 Hz), 7.12(2H, d, J=9.0 Hz).

Also, by purifying the residue by silica gel column chromatography (eluent: benzene), 32.76 g of the monoketone substance A was recovered.

EXAMPLE 2

Preparation of 1-[β-(2',4'-dimethylphenyl)-β-(4'-dipropylaminophenyl)vinyl]-4-[β-(2',4'-dimethylphenyl)-β-(4'-dimethylaminophenyl)vinyl]benzene (Illustrative Compound 2)

In a 0.5 liter reaction flask were placed 1.9 g (0.0792 mol) of magnesium and 20 ml of dry THF under a nitrogen atmosphere, and then small amounts of iodine and ethyl bromide were added to the mixture. After confirming the initiation of the reaction, a solution obtained by dissolving 15.52 g (0.0776 mol) of N,N-dimethyl-p-bromoaniline in 100 ml of dry toluene was added dropwise to the mixture at room temperature over a period of one hour to provide a Grignard reagent.

Then, to the reaction mixture was added dropwise a mixture of 20.5 g (0.0388 mol) of the monoketone substance A, (1-[β-(2',4'-dimethylphenyl)-β-(4'-dipropylaminophenyl)vinyl]-4-(2',4'-dimethylbenzoylmethyl)benzene) synthesized in Comparative Example 1 and 200 ml of dry toluene at room temperature over a period of 2 hours. Thereafter, the reaction was carried out with stirring for 18 hours at room temperature and the reaction mixture was post-treated as in Example 1 to provide 4.41 g of a crude product. By recrystallizing the crude product from ethyl acetate, 3.98 g of 1-[β-(2',4'-dimethylphenyl)-β-(4'-dipropylaminophenyl)vinyl]-4-[β-(2',4'-dimethylphenyl)-β-(4'-dimethylaminophenyl)vinyl]benzene (Illustrative Compound 2) was obtained.

M.p.: 190° C. to 191° C.

MASS (m/z): 632 ($M^+$)

$^1$H-NMR (400 MHz, δppm, $CDCl_3$): 0.90(6H, t, J=7.4 Hz), 1.58(4H, m), 1.96(3H, s), 1.97(3H, s), 2.36(3H, s), 2.37(3H, s), 2.93(6H, s), 3.21(4H, t, J=7.7 Hz), 6.53(2H, d, J=9.0 Hz), 6.63(2H, d, J=9.0 Hz), 6.64(4H, s), 6.80(1H, s), 6.81(1H, s), 6.95(2H, d, J=7.6 Hz), 6.99(2H, d, J=7.7 Hz), 7.03(2H, s), 7.11(2H, d, J=9.0 Hz), 7.15(2H, d, J=9.0 Hz).

Comparative Example 2

Preparation of 1-[β-(2',4'-dimethylphenyl)-β-(4'-diethylaminophenyl)vinyl]-4-(2',4'-dimethylbenzoylmethyl)benzene and 1,4-bis[β-(2',4'-dimethylphenyl)-β-(4'-diethylaminophenyl)vinyl]benzene (Comparative Compound 2)

In 2 liter reaction flask were placed 9.8 g (0.4 mol) of magnesium and 20 ml of dry THF under a nitrogen atmosphere, and small amounts of iodine and ethyl bromide were added to the mixture. After confirming the initiation of the reaction, a solution of 91.2 g (0.4 mol) of N,N-diethyl-p-bromoaniline in 400 ml of dry THF was added dropwise to the mixture at a temperature of from 25° C. to 35° C. over a period of 2 hours. Thereafter, the reaction was carried out for 18 hours at room temperature to provide a Grignard reagent.

Then, to the reaction mixture was added dropwise a mixed solution of 74 g (0.2 mol) of 1,4-bis(2',4'-dimethylbenzoylmethyl)benzene synthesized in Synthesis Example and 400 ml of dry toluene at a temperature from −30° C. to −40° C. over a period of 2 hours and then the reaction was carried out for 3 hours at the same temperature. Thereafter, the reaction mixture was poured into an aqueous 5% ammonium chloride solution followed by stirring for 30 minutes. Thereafter, the product was extracted with toluene, washed with an aqueous sodium chloride solution (1.5 liters, twice, pH after washing was 7), dried with anhydrous magnesium sulfate, and concentrated to provide 158 g of crude product. The crude product was recrystallized (−20° C.) from 316 g of ethanol to remove 53.1 g of unreacted 1,4-bis(2',4'-dimethylbenzoylmethyl)benzene.

The residual mother liquor was concentrated and after adding thereto 0.5 g of PTSA and 500 ml of toluene, an azeotropic dehydration was carried out for 2 hours under refluxing and stirring. After cooling the solution, the solution was washed with an aqueous sodium chloride solution, washed with an aqueous 5% sodium carbonate solution, and washed again with an aqueous sodium chloride solution, dried, concentrated, and distilled (boiling point to 87° C./1 mmHg, bath temperature to 160° C.) by a vigreux distilling column to remove 52.4 g of N,N-diethylaniline, whereby 51.1 g of a residue was obtained. The residue was purified by silica gel column chromatography (eluent: benzene) to provide 4 g of (oily) 1-[β-(2',4'-dimethylphenyl)-β-(4'-diethylaminophenyl)vinyl]-4-(2',4'-dimethylbenzoylmethyl)benzene.

MASS (m/z): 501 ($M^+$), 368, 133

IR (neat, $cm^{-1}$): 1680 (C=O)

$^1$H-NMR (400 MHz, δppm, $CDCl_3$): 1.14(6H, t, J=7.1 Hz), 2.00(3H, s), 2.32(3H, s), 2.36(3H, s), 2.40(3H, s), 3.33(4H, t, J=7.6 Hz), 6.58(2H, d, J=8.9 Hz), 6.85(2H, d, J=8.3 Hz), 6.89(1H, s), 6.95(2H, d, J=8.3 Hz), 6.98 to 7.04(5H, m), 7.16(2H, d, J=8.9 Hz), 7.59(1H, d, J=8.4 Hz).

Also, by silica gel column chromatography (eluent:benzene) described above, 7.0 g of the crude crystals of 1,4-bis[β-(2',4'-dimethylphenyl)-β-(4'-diethylaminophenyl)vinyl]benzene (Comparative Compound 2) were also obtained. The crude crystals were recrystallized from a mixed solvent of ethanol and ethyl acetate to provide 3.9 g of pure 1,4-bis [β-(2',4'-dimethylphenyl)-β-(4'-diethylaminophenyl)vinyl]benzene (Comparative Compound 2).

M.p.: 234° C. to 236° C.

MASS (m/z): 632 ($M^+$)

$^1$H-NMR (400 MHz, δppm, $CDCl_3$): 1.14(12H, t, J=7.0 Hz), 1.98(6H, s), 2.37(6H, s), 3.33(8H, q, J=7.0 Hz), 6.57 (4H, d, J=9 Hz), 6.64(4H, s), 6.80(2H, s), 6.95(2H, d, J=7.6 Hz), 6.99(2H, d, J=7.6 Hz), 7.12(4H, d, J=7.0 Hz).

EXAMPLE 3

Preparation of 1-[β-(2',4'-dimethylphenyl)-β-(4'-diethylaminophenyl)vinyl]-4-[β-(2',4'-dimethylphenyl)-β-(4'-dimethylaminophenyl)vinyl]benzene (Illustrative Compound 1)

In a 200 ml reaction flask were placed 0.48 g (20 mmols) of magnesium and 5 ml of dry THF under a nitrogen atmosphere and then small amounts of iodine and ethyl bromide were added to the mixture. After confirming the initiation of the reaction, a mixture of 4.0 g (20 mmols) of N,N-dimethyl-p-bromoaniline and 50 ml of dry THF was added dropwise to the mixture at room temperature over a period of 0.5 hour and then the reaction was carried out for 3 hours at the same temperature to provide a Grignard reagent.

Then, a mixed solution of 1.82 g (4.28 mmols) of 1-[β-(2',4'-dimethylphenyl)-β-(4'-diethylaminophenyl)vinyl]-4-(2',4'-dimethylbenzoylmethyl)benzene synthesized in Comparative Example 2 and 50 ml of dry toluene was added dropwise to the reaction mixture at a temperature of from 23° C. to 30° C. over a period of 0.5 hour and then the reaction was carried out for 19 hours at room temperature. Thereafter, the reaction mixture was poured into 600 g of an ice-cold aqueous 5% ammonium chloride solution and after stirring for 30 minutes, the solution containing the product was separated, washed with an aqueous sodium chloride solution, dried with anhydrous magnesium sulfate, and concentrated to provide 5.3 g of crude 1-[β-(2',4'-dimethylphenyl)-β-(4'-diethylaminophenyl)vinyl]-4-[2-hydroxy-2-(2',4'-dimethylphenyl)-2-(4'-dimethylaminophenyl)ethyl]benzene shown below.

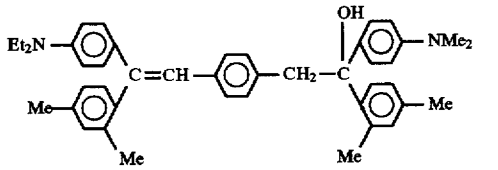

Then, after adding 100 ml of toluene and 0.2 g of PTSA to the reaction mixture, the mixture was subjected to an azeotropic dehydration reaction under refluxing for 2 hours. The reaction mixture was cooled, washed with an aqueous sodium chloride solution, washed with an aqueous 1% sodium carbonate solution, washed again with an aqueous sodium chloride solution, dried, and concentrated to provide 4.4 g of a residue. By purifying the residue by silica gel column chromatography (eluent:benzene), 2.0 g of a crude product was obtained. The crude product was further recrystallized from ethyl acetate to provide 0.5 g of 1-[β-(2',4'-dimethylphenyl)-β-(4'-diethylaminophenyl)vinyl]-4-[β-(2',4'-dimethylphenyl)-β-(4'-dimethylaminophenyl)vinyl] benzene (Illustrative Compound 1):

M.p.: 195° C. to 196° C.

MASS (m/z): 604 ($M^+$)

$^1$H-NMR (400 MHz, δppm, $CDCl_3$): 1.14(6H, t, J=7.0 Hz), 1.96(3H, s), 1.98(3H, s), 2.37(6H,s), 2.93(6H, s), 3.33(4H, t, J=7.0 Hz), 6.56(2H, d, J=9.0 Hz), 6.63(2H, d, J=9.0 Hz), 6.64(4H, s), 6.80(1H, s), 6.95(2H, d, J=7.6 Hz), 6.97(2H, d, J=7.7 Hz), 7.03(2H, s), 7.12(2H, d, J=9.0 Hz), 7.15(2H, d, J=9.0 Hz).

TEST EXAMPLE 1

Each of Illustrative Compounds 4, 2, and 1 and Comparative Compounds 1 and 2 obtained in Examples and Comparative Examples described above was subjected to a thermal analysis using a differential scanning calorimeter (DSC) for determining the glass transition temperature (Tg), the crystallization temperature (Tc) and the melting point (Tm). That is, when the temperature of each of the foregoing compounds was increased at a rate of 5° C./minute, an endothermic peak by melting of the compound was observed. The isotropic liquid obtained by melting in this case was quickly cooled by liquid nitrogen to form a transparent glassy compound. Then, when the temperature of the glassy compound was increased again at a rate of 5° C./minute, a glass transition point was seen and the temperature at the case was defined as the glass transition temperature (Tg) of the compound. Thereafter, when the temperature was further increased, an exothermic peak by crystallization was observed and the temperature at the case was defined as the crystallization temperature (Tc) of the compound. When the temperature was further increased, an endothermic peak by melting was observed and the temperature at the case was defined as the melting point (Tm) of the compound.

The results obtained are shown in Table 2 below.

TABLE 2

| Illustrative Compound | Tg (°C.) | Tc (°C.) | Tm (°C.) | Tc-Tg (°C.) | Tm-Tc (°C.) |
|---|---|---|---|---|---|
| 4 | 65.3 | —*** | 126.6 | — | — |
| 2 | 67.0 | 149.7 | 185.0 | 82.7 | 35.3 |
| 1 | 76.9 | 160.7 | 186.9 | 83.8 | 26.2 |
| C-1* | 58.9 | 125.2 | 166.3 | 66.3 | 41.1 |
| C-2** | 74.5 | 77.3 | 223.5 | 2.8 | 146.2 |

*Comparative Compound 1
**Comparative Compound 2
***The crystallization temperature could not be measured. That is, the compound was not crystallized.

From the results shown above, it can be seen that in Illustrative Compounds 4, 2, and 1 of the present invention, the values of Tc and (Tc–Tg) are larger than those of Comparative Compounds 1 and 2 and the value of (Tm–Tc) is smaller than that of the latter compounds. In other words, it can be seen that in the case of forming a film or layer, the compounds of the present invention are reluctant to cause crystallization.

APPLICATION EXAMPLES 1 AND 2

A mixture of 1 part by weight of τ type metal-free phthalocyanine and 1 part by weight of a butyral resin (Polyvnylbutyral BM-1, trade name, made by Sekisui Chemical Co., Ltd.) was kneaded using 30 parts by weight of tetrahydrofuran as a solvent in a ball mill for 5 hours. The pigment dispersion thus obtained was coated on a sheet formed by vapor-depositing aluminum on a polyethylene terephthalate (PET) film and dried for 2 hours at 100° C. to form a charge generating layer.

Apart from this, 1 part by weight of each of Illustrative Compounds 4, and 2 obtained in Examples 1 and 2 and 1 part by weight of a polycarbonate resin (Polycarbonate Z, trade name, made by Mitsubishi Gas Chemical Company, Inc.) were mixed and dissolved in 8 parts by weight of dichloroethane. Each of the solutions thus obtained was coated on the charge generating layer by a doctor blade and dried for 3 hours at 80° C. to form each charge transporting layer.

The electrophotographic characteristics of each of the electrophotographic photoreceptors thus obtained were measured by a static process using an electropaper analyzer, Type SP-428 (trade name, manufactured by Kawaguchi Denki Seisakusho K.K.).

That is, each photoreceptor was electrostatically charged by corona discharge at −6 kV for 5 seconds and the surface potential $V_o$ (unit: −volt) was measured. Then, after placing the photoreceptor in the dark for 5 seconds, the photoreceptor was irradiated by light of 5 lux emitted from a tungsten lamp, and the light-exposure amount necessary for decaying the surface potential to a half, that is, a half decay light-exposure amount $E_{1/2}$ (lux.second) and the surface residual potential $V_{R10}$ (−volt) after irradiating the photoreceptor for 10 seconds by light of 5 lux in the illuminance were measured. The results are shown in Table 3 below.

APPLICATION EXAMPLE 3

By following the same procedure as Application Examples 1 and 2 except that x type phthalocyanine was used in place of τ type phthalocyanine and Illustrative Compound 1 prepared in Example 3 was used in place of Illustrated Compounds 4 and 2, an electrophotographic photoreceptor was prepared and the elecrtrophotographic characteristics thereof were measured. The results are shown in Table 3 below.

TABLE 3

| Application Example | $V_0$ (−V) | $V_{R10}$ (−V) | $E_{1/2}$ (lux · sec) |
|---|---|---|---|
| 1 | 998 | 0 | 0.9 |
| 2 | 940 | 0 | 0.7 |
| 3 | 960 | 0 | 0.9 |

From the results shown above, it can be seen that in Application Examples 1 to 3 using the compounds of the present invention, the surface residual potential $V_{R10}$ after irradiating light for 10 seconds is 0 volt in each case, whereby the compounds of the present invention are excellent in the charge transportability.

APPLICATION EXAMPLES 4 TO 6

After mixing and dissolving 1 part by weight of each of Illustrative Compounds 4, 2, and 1 obtained in Examples 1, 2, and 3 and 1 part by weight of a polycarbonate resin in 8 parts by weight of dichloroethane, each solution thus obtained was coated on a sheet formed by vapor-depositing aluminum on a polyethylene terephthalate (PET) film by a doctor blade and dried for 3 hours at 80° C. to form a charge transporting layer.

Furthermore, a translucent metal (Au) electrode was vapor-deposited on each of the charge transporting layers and the carrier drift mobilities were measured.

The measurement of the carrier drift mobility was carried by a time-of-flight method [Soumei Tanaka, Yasuhiro Yamaguchi, and Masaaki Yokoyama, *Denshishashin* (*Electrophotography*), 29, 366(1990)] using a nitrogen gas laser having a pulse half value width of 0.9 nsec and a wavelength of 337 nm as the light source.

The results obtained are shown in Table 4 below.

TABLE 4

| Application Example | Illustrative Compound | Carrier Drift Mobility ($10^{-6}$ $cm^2$ $V^{-1}$ $s^{-1}$) |
|---|---|---|
| 4 | 4 | 15.5 |
| 5 | 2 | 86.9 |
| 6 | 1 | 8.58 |

From the results shown above, it can be seen that usually if the carrier drift mobility of a charge transporting layer is about 8 to $9\times10^{-6}$ ($cm^2$/Vs), the charge transporting layer is considered to be excellent, while by using the compounds of the present invention, a higher carrier drift mobility is obtained.

APPLICATION EXAMPLE 7

In the case of dissolving Illustrative Compound 4 obtained in Example 1 in a polycarbonate resin as a binder, the compound was added to a polycarbonate resin in a weight ratio of 30%, 50%, 70%, or 80% to the whole mixture and was mixed therewith and dissolved therein with dichloroethane of 4 times (by weight) the amount of the solid components. In these cases, the compound was uniformly dissolved and the solubility of the charge transporting material was high.

Each solution was coated on a sheet formed by vapor-depositing aluminum on a polyethylene terephthalate (PET) film by the same manner as in Application Examples 1 and 2 except that x type phthalocyanine was used in place of τ type phthalocyanine and the mixture prepared above was used as the charge transporting material, and dried for 3 hours at 80° C. to form each charge transporting layer. When the charge transporting layer containing the charge transporting material at a high concentration as described above, the uniform layer having neither deposition of crystals nor the formation of pinholes could be formed.

Then, a translucent metal (Au) electrode was vapor-deposited on each of the charge transporting layers and the carrier mobilities were measured. The results are shown in table 5 below.

Furthermore, 100% Illustrative Compound 4 without using a binder was mixed with and dissolved in dichloroethane in an amount of twice (by weight) the amount of the solid material and the solution was added dropwise onto the foregoing sheet by a Pasteur pipet. After drying at room temperature, the layer was further dried at 80° C. for 3 hours under reduced pressure to form a charge transporting layer.

As described above, when the charge transporting layer composed of the charge transporting material only without the addition of a binder was formed, a uniform layer having neither the deposition of crystals nor the formation of pinholes could be formed.

The carrier drift mobility was measured by the same manner as above and the result is shown in Table 5 below.

TABLE 5

(Mobility Change to Concentration of Illustrative Compound 4)

| Weight % | Carrier Drift Mobility ($10^{-6}$ $cm^2$ $V^{-1}$ $s^{-1}$) |
|---|---|
| 30 | 2.15 |
| 50 | 15.5 |
| 70 | 34.2 |
| 80 | 49.1 |
| 100 | 63.0 |

From the results shown above, it can be seen that in the case of using the compound of the present invention at 100%, the high carrier drift mobility of $63\times10^{-6}$($cm^2$/Vs) can be obtained and thus the compound of the present invention is very useful.

APPLICATION EXAMPLE 8

In the case of dissolving Illustrative Compound 2 obtained in Example 2 in a polycarbonate resin, the compound was added such that the weight ratio of Illustrative Compound 2 became 50% or 90% of the whole mixture and the compound was mixed with and dissolved in the polycarbonate resin with dichloroethane of 4 times (by weight) the total weight of the solid components. The compound was uniformly dissolved in each case and solubility of the charge transporting material was high.

Each of the solutions was coated on a sheet obtained by vapor-depositing aluminum on a polyethylene terephthalate (PET) film by the same manner as Application Examples 1 and 2 except that x type phthalocyanine was used in place of τ type phthalocyanine and each of the mixture prepared above was used as the charge transporting material, and dried for 3 hours at 80° C. to form a charge transporting layer.

When the charge transporting layer containing the charge transporting material of the present invention at such a high concentration was formed, a uniform layer having neither the deposition of crystals nor the formation of pinholes could be formed.

Then, a translucent metal (Au) electrode was formed on each of the charge transporting layers by vapor-deposition and the carrier drift mobility thereof was measured. The results obtained are shown in Table 6 below.

TABLE 6

(Mobility Change to Concentration of Illustrative Compound 2)

| Weight % | Carrier Drift Mobility ($10^{-6}$ $cm^2$ $V^{-1}$ $s^{-1}$) |
|---|---|
| 50 | 86.9 |
| 90 | 91.6 |

COMPARATIVE APPLICATION EXAMPLE 1

In the case of dissolving Comparative Compound 1 obtained in Comparative Example 1 in a polycarbonate resin as a binder, the compound was added such that the weight ratio of Comparative Compound 1 became 20%, 30%, 50%, or 70% of the whole mixture and mixed and dissolved with dichloroethane of 4 times (by weight) the amount of the solid components.

Each of the solutions obtained was coated on a sheet formed by vapor-depositing aluminum on a polyethylene terephthalate (PET) film by the same manner as Application Examples 1 and 2 except that x type phthalocyanine was used in place of τ type phthalocyanine and each of the mixed and dissolved products described above was used as the charge transporting material followed by drying at 80° C. for 3 hours.

The results showed that when the weight ratio of Comparative Compound was 20%, 30%, and 50%, uniform coated layers were obtained but when the weight ratio thereof was 70%, crystals deposited on the whole surface of the coated layer.

Then, a translucent metal (Au) electrode was vapor-deposited on each of the charge transporting layers and the carrier drift mobilities were measured in each case (in the case of 70%, the carrier drift mobility could not be measured owing to the deposition of crystals). The results obtained are shown in Table 7 below.

TABLE 7

(Mobility Change to Concentration of Comparative Compound 1)

| Weight % | Carrier Drift Mobility ($10^{-6}$ $cm^2$ $V^{-1}$ $s^{-1}$) |
|---|---|
| 20 | 0.51 |
| 30 | 1.23 |
| 50 | 9.52 |
| 70 | Crystal deposited |

From the results shown above, it can be seen that in the case of using Comparative Compound 1, when the weight ratio of the compound was 70%, crystals deposited and also when the weight ratio of the compound was until 50%, uniform coated layers were obtained but the carrier drift mobilities of the coated layers were insufficient as compared with the cases in Application Examples 7 and 8.

COMPARATIVE APPLICATION EXAMPLE 2

In the case of dissolving Comparative Compound 2 obtained in Comparative Example 2 in a polycarbonate resin as a binder, the compound was added such that the weight ratio of Comparative Compound 2 became 20%, 30%, 40%, 50%, 60%, 70%, or 80% of the whole mixture and the compound was mixed with and dissolved in the polycarbonate resin with dichloroethane of 4 times (by weight) the amount of the solid components.

Each of the solutions was coated on a sheet formed by vapor-depositing aluminum on a polyethylene terephthalate (PET) film by the same manner as in Application Examples 1 and 2 except that x type phthalocyanine was used in place of τ type phthalocyanine and each of the mixed and dissolved products decribed above was used as the charge transporting material followed by drying at 80° C. for 3 hours.

The results showed that when the weight ratio of the compound was 20% to 70%, uniform coated layers were obtained but when the weight ratio was 80%, crystals deposited on the whole surface of the coated layer.

Then, a translucent metal (Au) electrode was vapor-deposited on each of the charge transporting layers and the carrier drift mobilities were measured (when the weight ratio was 80%, the carrier drift mobility could not be measured owing to the deposition of the crystals). The results obtained are shown in Table 8.

TABLE 8

(Mobility Change to Concentration of Comparative Compound 2)

| Weight % | Carrier Drift Mobility ($10^{-6}$ $cm^2$ $V^{-1}$ $s^{-1}$) |
|---|---|
| 30 | 1.17 |
| 40 | 4.43 |
| 50 | 11.7 |
| 60 | 16.0 |
| 70 | 18.3 |
| 80 | Crystal deposited |

From the results shown above, it can be seen that in the case of using Comparative Compound 2, when the weight ratio of the compound was 80%, crystals deposited and also when the weight ratio was until 70%, uniform coated layers were obtained but the carrier mobilities of the coated layers were insufficient as compared with the cases of Application Examples 7 and 8.

As described above, the 1,4-bis(2',2'-diphenylvinyl) benzene derivative (I) of the present invention has a good solubility and when a film or layer containing the compound at a high concentration is formed by increasing the addition amount of the compound, a uniform and stabilized film or layer having an excellent faculty as a charge transporting material can be formed. Thus, when an electrophotographic photoreceptor is prepared using the compound of the present invention for the charge transporting layer, the charge transporting layer can show a high carrier drift mobility and the electrophotographic photoreceptor has good characteristics of a high sensitivity and giving no residual potential. Thus, the compound (I) of the present invention is an industrially excellent compound.

While the invention has been described in detail and with reference to specific embodiments thereof, it will be apparent to one skilled in the art that various changes and modifications can be made therein without departing from the spirit and scope thereof.

What is claimed is:

1. A 1,4-bis(2',2'-diphenylvinyl)benzene derivative represented by formula (I):

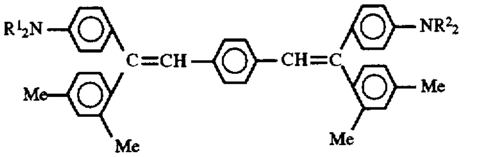

(I)

wherein $R^1$ and $R^2$ each represents a different lower alkyl group and Me represents a methyl group.

2. A 1,4-bis(2'2'-diphenylvinyl)benzene derivative as in claim 1, wherein the different lower alkyl group has from 1 to 4 carbon atoms.

3. A 1,4-bis(2'2'-diphenylvinyl)benzene derivative as in claim 1, wherein the different lower alkyl group is selected from methyl, ethyl, propyl and n-butyl.

4. A 1,4-bis(2'2'-diphenylvinyl)benzene derivative as in claim 1, wherein $R^1$ is an ethyl group and $R^2$ is a propyl group.

5. A 1,4-bis(2'2'-diphenylvinyl)benzene derivative as in claim 1, wherein $R^1$ is a methyl group and $R^2$ is a propyl group.

6. A 1,4-bis(2'2'-diphenylvinyl)benzene derivative as in claim 1, wherein $R^1$ is a methyl group and $R^2$ is an ethyl group.

7. A charge transporting material comprising a 1,4-bis(2',2'-diphenylvinyl)benzene derivative represented by formula (I):

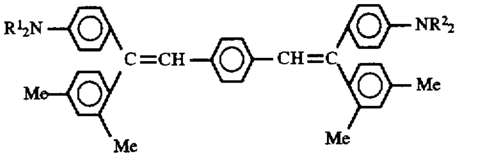

(I)

wherein $R^1$ and $R^2$ each represents a different lower alkyl group and Me represents a methyl group.

8. A charge transporting material as in claim 7, wherein the different lower alkyl group has from 1 to 4 carbon atoms.

9. A charge transporting material as in claim 7, wherein the different lower alkyl group is selected from methyl, ethyl, propyl and n-butyl.

10. A charge transporting material as in claim 7, wherein $R^1$ is an ethyl group and $R^2$ is a propyl group.

11. A charge transporting material as in claim 7, wherein $R^1$ is a methyl group and $R^2$ is a propyl group.

12. A charge transporting material as in claim 7, wherein $R^1$ is a methyl group and $R^2$ is an ethyl group.

* * * * *